United States Patent [19]

Cooper

[11] 4,379,841
[45] Apr. 12, 1983

[54] ASSIMILATION TEST FOR IDENTIFYING YEASTS

[75] Inventor: Billy H. Cooper, Dallas, Tex.

[73] Assignee: Abbott Laboratories

[21] Appl. No.: 308,210

[22] Filed: Oct. 2, 1981

Related U.S. Application Data

[63] Continuation-in-part of Ser. No. 184,877, Sep. 8, 1980, abandoned.

[51] Int. Cl.$^3$ .................... C12Q 1/04; C12N 1/16; C12R 1/645; C12R 1/72
[52] U.S. Cl. .................... 435/34; 435/255; 435/911; 435/921; 435/922
[58] Field of Search ............. 435/34, 921, 922, 254, 435/255, 256, 911

[56] References Cited

U.S. PATENT DOCUMENTS 4,030,980  6/1977  Beckford et al. ............. 435/34 X
4,140,580  2/1979  Gibson et al. ............... 435/921 X

OTHER PUBLICATIONS

Edwin H. Lennette et al., Editors, *Manual of Clinical Microbiology*, 2nd Ed., pp. 496–497; 1974.
*J. Gen. Microbiol.*, 20:13–23 (1959).
*Sven. Papperstidn.*, 72:531–536 (1969).
*Nature*, 195:473–474 (1962).
*J. Gen. Microbiol.*, 26:149–154 (1961).
*Antonie van Leevwenhoek*, J. Microbiol. Serol., 37:303–312 (1971).
*Experientia*, 24:844–845 (1968).
J. P. Van der Walt from J. Lodden (ed.) *The Yeasts, A Taxanomic Study*, 2nd Edition, (1970) 75–83.
*J. Bacteriology*, 56:363–371 (1948).
*Manual of Clinical Microbiology*, 3rd Edition, Yeasts of Medical Importance, pp. 562–576, American Society for Microbiology, Washington.

*Primary Examiner*—Robert J. Warden
*Attorney, Agent, or Firm*—Steven M. Odre; John J. McDonnell

[57] ABSTRACT

The disclosure relates to a culture medium containing as a sole carbon source 4-hydroxybenzoic acid, 3,4-dihydroxybenzoic acid or a mixture thereof, and to an assimilation test for identifying yeasts utilizing such a culture medium.

12 Claims, No Drawings

ASSIMILATION TEST FOR IDENTIFYING YEASTS

This invention is a continuation-in-part of application Ser. No. 184,877, filed Sept. 8, 1980 now abandoned.

BACKGROUND OF THE INVENTION

1. Field Of The Invention

The present invention relates to a novel yeast culture medium and to an assimilation test procedure employing such medium which is useful in conjunction with known conventional procedures presently employed to identify specific clinically significant species of yeast in an unknown isolate. The procedure of the present invention is particularly useful in distinguishing *Candida parapsilosis* from other *Candida* species and *Cryptococcus neoformans* from other *Cryptococcus* species.

2. Description Of The Prior Art

Conventional methods utilized to identify yeasts include tests for assimilation of carbohydrates, nitrogen sources, and in some instances, fatty acids or alkanes along with a variety of other tests.

The ability of yeasts and other fungi to metabolize phenolic compounds has been regarded as unique characteristic of certain isolates that might be exploited for reducing the phenolic content of sewage and other waste materials. *J. Gen. Microbiol*, 20:13-23 (1959); Sven. Papperstidn. 72:531-536 (1969); *Nature*, 195:473-474 (1962); *J. Gen. Microbiol.*, 26:149-154 (1961) and Antonie van Leevwenhoek, *J. Microbiol. Serol.*, 37:303-312 (1971). However, these references fail to teach or suggest the utilization of a particular phenolic compound as a sole carbon-source in a culture medium utilized in procedures for differentiating yeast species.

Kunze, *Experientia*, 24:844-845 (1968), identified nine phenolic compounds derived from the decomposition of lignin, including vanillin (4-hydroxy-3-methoxybenzaldehyde), vanillic acid (4-hydroxy-3-methoxybenzoic acid), 4-hydroxybenzaldehyde, PHBA (4-hydroxybenzoic acid), ferulic acid (4-hydroxy-3-methoxycinnamic acid), coumaric acid (4-hydroxycinnamic acid), protocatechuic acid; PCA (3,4-dihydroxybenzoic acid), caffeic acid (3,4-dihydroxycinnamic acid), and gallic acid (3,4,5-trihydroxybenzoic acid). However, no utility was disclosed or suggested for the compounds identified by Kunze.

SUMMARY OF THE INVENTION

The present invention relates to a method for identifying a clinically significant yeast isolate which comprises inoculating a culture medium containing a sole carbon source 4-hydroxybenzoic acid, 3,4-dihydroxybenzoic acid or a mixture of 4-hydroxybenzoic acid and 3,4-dihydroxybenzoic acid, with a yeast colony obtained from human specimen; and then observing the ability of the yeast colony to assimilate the carbon source as an indication of a specific yeast isolate.

The present invention further relates to an improved culture medium useful in assimilation test procedures for yeasts, the improvement comprises 4-hydroxybenzoic acid, 3,4-dihydroxybenzoic acid or a mixture of 4-hydroxybenzoic acid and 3,4-dihydroxybenzoic acid, as a sole carbon source in the culture media.

DESCRIPTION OF THE PREFERRED EMBODIMENTS

The term "clinically significant yeasts" includes yeasts generally associated with human disease. Illustrative of such clinically significant yeasts include *Candida albicans, Candida guilliermodii, Candida krusei, Candida parapsilosis, Candida pseudotropicalis, Candida stellatoidea, Candida tropicalis, Cryptococcus neoformans*, and the like.

A preferred aspect of the medium and methods of the present invention is the ability to distinguish *Candida parapsilosis* from other *Candida* species. It is more preferred to employ the medium and methods of the present invention to distinquish *Candida parapsilosis* from *Candida albicans*.

Another preferred aspect of the medium and methods of the present invention is the ability to distinguish *Cryptococcus neoformans* from *Cryptococcus albidus, Cryptococcus laurentii* and *Cryptococcus terreus*. It is more preferred to employ the medium and methods of the present invention to distinguish *Cryptococcus neoformans* from *Cryptococcus albidus*.

Procedures for preparing and using the media employed in the method of the present invention are generally well known to one having ordinary skill in the art. In addition to a carbon-source containing 4-hydroxybenzoic acid and/or 3,4-dihydroxybenzoic acid, the media of the present invention comprises a Bacto-yeast nitrogen base as a basal medium. Components of a typical yeast nitrogen base are listed on page 82, Table III of *The Yeast-A Taxonomic Study* by J. P. van der Walt (edited by J. Lodder), 2nd Edition (1970).

The term "effective amount of 4-hydroxybenzoic acid or 3,4-dihydroxybenzoic acid" refers to the quantity of the particular hydroxybenzoic acid sufficient to produce detectable assimilation when a culture medium containing the particular acid as a sole carbon source is inoculated with a yeast colony. The assimilation may be detected visually or by photometric means. Such quantities of 4-hydroxybenzoic acid and/or 3,4-dihydroxybenzoic acid effective in the medium of the present invention vary and are readily ascertained by one of ordinary skill in the art. It has been found that a concentration of the 4-hydroxybenzoic acid and/or 3,4-dihydroxybenzoic acid of approximately 0.01M is generally sufficient.

In order to increase the sensitivity of the detecting growth, an indicator may be incorporated into the medium. Growths on slants containing 4-hydroxybenzoic acid or 3,4-dihydroxybenzoic acid produce a shift to a more alkaline pH in the growth media. For example, if bromothymol blue is employed as the indicator, the color of the indicator will change from yellow to green or blue. The change of the indicator color may be visully observed or monitored by photometric detection apparatus.

The following example serves to further illustrate the present invention. The techniques employed in the media preparation and culture growth procedures of the following Example are generally well known to one of ordinary skill in the art.

EXAMPLE

Materials and Methods

A total of 451 isolates, including recent clinical isolates and reference strains obtained from the American Type Culture Collection and othe culture collections, were evaluated. A majority of the isolates were originally obtained from clinical material from hospitalized patients that was submitted to a clinical mycology laboratory for diagnostic purposes. A few isolates from soil and other natural sources were also included, and at least one reference strain of each species tested, including the type strain of *Candida parapsilosis* was also evaluated.

Preparation of Media

Wickerham's yeast nitrogen bas (YNB; Difco Laboratories) was used as a basal medium for all test cultures, media and controls. The test media were prepared by incorporating 4-hydroxybenzoic acid or 3,4-dihydroxybenzoic acid as a sole carbon source into the yeast nitrogen base. In addition, for each test, a growth control tube containing yeast nitrogen base and a 0.5% glucose solution as a carbon source and a negative control tube containing only yeast nitrogen base were inoculated along with the test media containing 4-hydroxybenzoic acid or 3,4-hydroxybenzoic acid.

The culture media of the present invention were prepared by dissolving 2.76 g of 4-hydroxybenzoic acid (or 3.08 g of 3,4-dihydroxybenzoic acid) in approximately 25 ml of 1N sodium hydroxide and then adjusting the pH of the resulting solution to pH 7.5 using 1M hydrochloric acid. The pH 7.5 solution was then mixed with 100 ml of 10x yeast nitrogen base in deionized water containing 0.1% bromothymol blue indicator. The pH of the resultant mixture was adjusted to within a pH range of 6.0 to 6.5 and then diluted to 200 ml with deionized water. Stock solutions were prepared by sterilizing the diluted mixture by filtration. The stock solutions were stored at 4° C. The test media were prepared as agar slants by incorporating 1 ml of the stock solution into 4.0 ml of 2% Nobel agar (Difco) that had been previously sterilized by autoclaving at 15 lbs (ca. 1.05 Kg/cm$^2$) of pressure for 15 minutes and then cooling to 50° C. in a water bath. The tubed media were cooled iln a slanted position and stored at 4° C. until used. The final concentration of the 4-hydroxybenzoic acid or 3,4-dihydroxybenzoic acid in the test media was 0.01M.

The growth control tube was prepared in accordance with the above-described procedure but substituting 10 g of glucose for the hydroxybenzoic acid. The final concentration of the glucose in the growth control medium was 0.5% by weight.

The negataive control tube was prepared in accordance with the above-described procedure but eliminating the carbon source, i.e., hydroxybenzoic acid.

Cultural Conditions

For inoculation, 0.1 ml of a slightly turbid suspension (+1, using Wickerham card) of a yeast isolate was added to the growth control tube, the negative control tube, 4-hydroxybenzoic acid containing tube and the 3,4-hydroxybenzoic acid containing tube. The inoculated tubes were incubated at 30° C. and examined at 48 hr. intervals for evidence of growth. All tubes were held for a total of 14 days before being recorded as negative.

The results obtained from the the foregoing procedure are represented in Table I. The values reported indicate the number of positive indentifications per total number of tests.

TABLE I

ASSIMILATION OF 4-HYDROXYBENZOIC ACID AND 3,4-DIHYDROXYBENZOIC ACID BY SELECTED YEAST ISOLATES

| Species Tested | 3,4-Dihydroxy benzoic acid | 4-Hydroxy benzoic acid |
| --- | --- | --- |
| *Candida albicans* | 0/46 | 0/46 |
| *Candida fuilliermondii* | 0/10 | 0/10 |
| *Candida humicola* | 5/5 | 5/5 |
| *Candida krusei* | 0/13 | 0/13 |
| *Candida parapsilosis* | 60/60 | 60/60 |
| *Candida pseudotropicalis* | 0/4 | 0/4 |
| *Candida stellatoidea* | 0/27 | 0/27 |
| *Candida tropicalis* | 0/58 | 0/58 |
| Miscellaneous *Candida* spp.* | 0/12 | 0/12 |
| *Cryptococcus albidus* | 55/56 | 55/56 |
| *Cryptococcus laurentii* | 11/24 | 11/24 |
| *Cryptococcus luteolus* | 0/1 | 0/1 |
| *Cryptococcus neoformans* | 0/29 | 0/29 |
| *Cryptococcus skinneri* | 0/1 | 0/1 |
| *Cryptococcus terreus* | 4/4 | 4/4 |
| *Cryptococcus uniguttalatus* | 0/2 | 0/2 |
| *Geotrichum* | 2/3 | 2/3 |
| *Rhodotorula glutinis* | 9/10 | 10/10 |
| *Rhodotorula graminis* | 1/1 | 1/1 |
| *Rhodotorula rubra* | 3/5 | 3/5 |
| *Saccharomyces cerevisiae* | 0/15 | 0/15 |
| *Torulopsis anatomiae* | 1/1 | 1/1 |
| *Torulopsis candida* | 0/5 | 0/5 |
| *Torulopsis glabrata* | 0/46 | 0/46 |
| *Trichosporon capitatum* | 0/2 | 0/2 |
| *Trichosporon cutaneum* | 9/10 | 10/10 |
| *Trichosporon pullulans* | 0/1 | 0/1 |

*Includes *C. aaseri, C. lipolytica, C. maltosa C. rugosa, C. utilis,* and *C. zeylanoides.*

The results in Table I illustrate the use of 4-hydroxybenzoic acid and 3,4-dihydroxybenzoic acid as the sole carbon source in assimilation tests employed in conjunction with conventional test for identifying isolates of *Candida parapsilosis,* some *Cryptococcus* species as well as other yeasts.

As evidenced by the results in Table I, of the fourteen *Candida* species tested, only *Candida parapsilosis* and *Candida humicola* were capable of assimilating 4-hydroxybenzoic acid and 3,4-dihydroxybenzoic acid. In view of the fact that *Candida humicola* is only rarely isolated from human patients, the method of the present invention provides a generally specific test for distinguishing *Candida parapilosis* from other *Candida* species which are clincally significant. In particular, the procedure of the present invention is a valuable test in distinguishing *Candida parapsilosis* from *Candida albicans* and *Candida tropicalis.* An important aspect of the present procedure is that it significantly reduces the time required for making a definitive identification of *Candida parapsilosis* when compared with conventional methodology. Techniques commonly employed heretofore to distinquish *Candida parapsilosis* from *Candida albicans* and *Candida tropicalis* comprise negative tests for assimilation of cellobiose and soluble starch in addition to negatve tests for fermentation of maltose and sucrose. By employing the media and procedures of the present invention, the time period for definitively indentifying *Candida parapsilosis* is significantly shortened since assimilation of 4-hydroxybenzoic acid and 3,4-dihydroxybenzoic acid is observed in a shorter period of time than is necessary to ascertain that negative assimilation and fermentation tests are actually negative.

The results in Table I further demonstrate that the procedures of the present invention are useful for differentiating *Cryptococcus neoformans,* the only clinically significant species of *Cryptococcus,* from contaminants

*Cryptococcus albidus, Cryptococcus terreus* and *Cryptococcus laurentii* in view of the fact that *Cryptococcus albidus, Cryptococcus terreus* and some isolates of *Cryptococcus laurentii* demonstrate positive assimilation of 4-hydroxybenzoic acid and 3,4-dihydroxybenzoic acid wherein *Cryptococcus neoformans* does not assimilate the carbon source.

The results obtained with *Cryptococcus neoformans* required careful evaluation. 4-Hydroxybenzoic acid and 3,4-dihydroxybenzoic acid reacted with phenol oxidase in the cell walls of individual *Cryptococcus neoformans* cells to produce a brown coloration of the inoculum, increasing its visibility and suggesting growth of these isolates; however, when compared with the growth control tube, it was obvious that little if any increase in cell numbers had occurred.

Although this invention has been described with respect to specific modifications, the details thereof are not construed as limitations, for it will be apparent that various equivalents, changes and modifications may be resorted to without departing from the spirit and scope thereof and it is understood that such equivalent embodiments are intended to be included herein.

What is claimed is:

1. A method for identifying a clinically significant yeast isolate which comprises inoculating culture media containing as a sole carbon source 4-hydroxybenzoic acid, 3,4-dihydroxybenzoic acid or a mixture of 4-hydroxybenzoic acid and 3,4-dihydroxybenzoic acid, with a yeast colony obtained from a human specimen; and then observing the ability of the yeast colony to assimilate the carbon source as an indication of a specific yeast isolate.

2. A method according to claim 1 wherein the yeast isolate to be identified is *Candida parapsilosis*.

3. A method according to claim 2 wherein the carbon source is 4-hydroxybenzoic acid.

4. A method according to claim 2 wherein the carbon source is 3,4-dihydroxybenzoic acid.

5. A method according to claim 1 wherein the yeast isolate to be identified is *Cryptococcus neoformans*.

6. A method according to claim 5 wherein the carbon source is 4-hydroxybenzoic acid.

7. A method according to claim 5 wherein the carbon source is 3,4-dihydroxybenzoic acid.

8. A method according to claim 1 wherein an indicator is added to the culture media.

9. A method according to claim 8 wherein the indicator is bromothymol blue.

10. A culture medium having application in assimilation test procedures for clinically significant yeast comprising an effective amount of 4-hydroxybenzoic acid, 3,4-dihydroxybenzoic acid or a mixture of 4-hydroxybenzoic acid and 3,4-dihydroxybenzoic acid as a sole carbon source in the culture medium.

11. A culture medium according to claim 10 wherein the sole carbon source is 4-hydroxybenzoic acid.

12. A culture medium according to Claim 10 wherein the sole carbon source is 3,4-dihydroxybenzoic acid.

* * * * *